United States Patent [19]

Barchas

[11] 4,116,999

[45] Sep. 26, 1978

[54] RECOVERY OF TEREPHTHALONITRILE

[75] Inventor: Richard K. Barchas, Upper Montclair, N.J.

[73] Assignee: The Lummus Company, Bloomfield, N.J.

[21] Appl. No.: 791,838

[22] Filed: Apr. 28, 1977

[51] Int. Cl.$^2$ .................. C07C 120/14; C07C 121/58
[52] U.S. Cl. .................. 260/465 H; 203/42; 203/60; 260/465 C
[58] Field of Search .................. 260/465 C, 465 H; 203/60

[56] References Cited

U.S. PATENT DOCUMENTS

| 3,206,378 | 9/1965 | Teramoto et al. | 202/42 |
| 3,732,275 | 5/1973 | Platz et al. | 260/465 H |
| 3,801,620 | 4/1974 | Hosler et al. | 260/465 C |

*Primary Examiner*—Dolph H. Torrence
*Attorney, Agent, or Firm*—Marn & Jangarathis

[57] ABSTRACT

Terephthalonitrile is separated from p-xylene containing solution by fractional distillation in the presence of p-tolunitrile, with the p-tolunitrile being present in the fractional distillation tower in an amount sufficient to solubilize the terephthalonitrile in all portions of the column at which the temperature in the column is below the melting point of tetephthalontrile, whereby terephthalonitrile can be recovered as a liquid. The solution generally includes p-xylene, benzonitrile, p-tolunitrile and terephthalonitrile and is separated from a terephthalonitrile production reaction effluent by direct contact quenching with an organic liquid containing p-tolunitrile.

9 Claims, 1 Drawing Figure

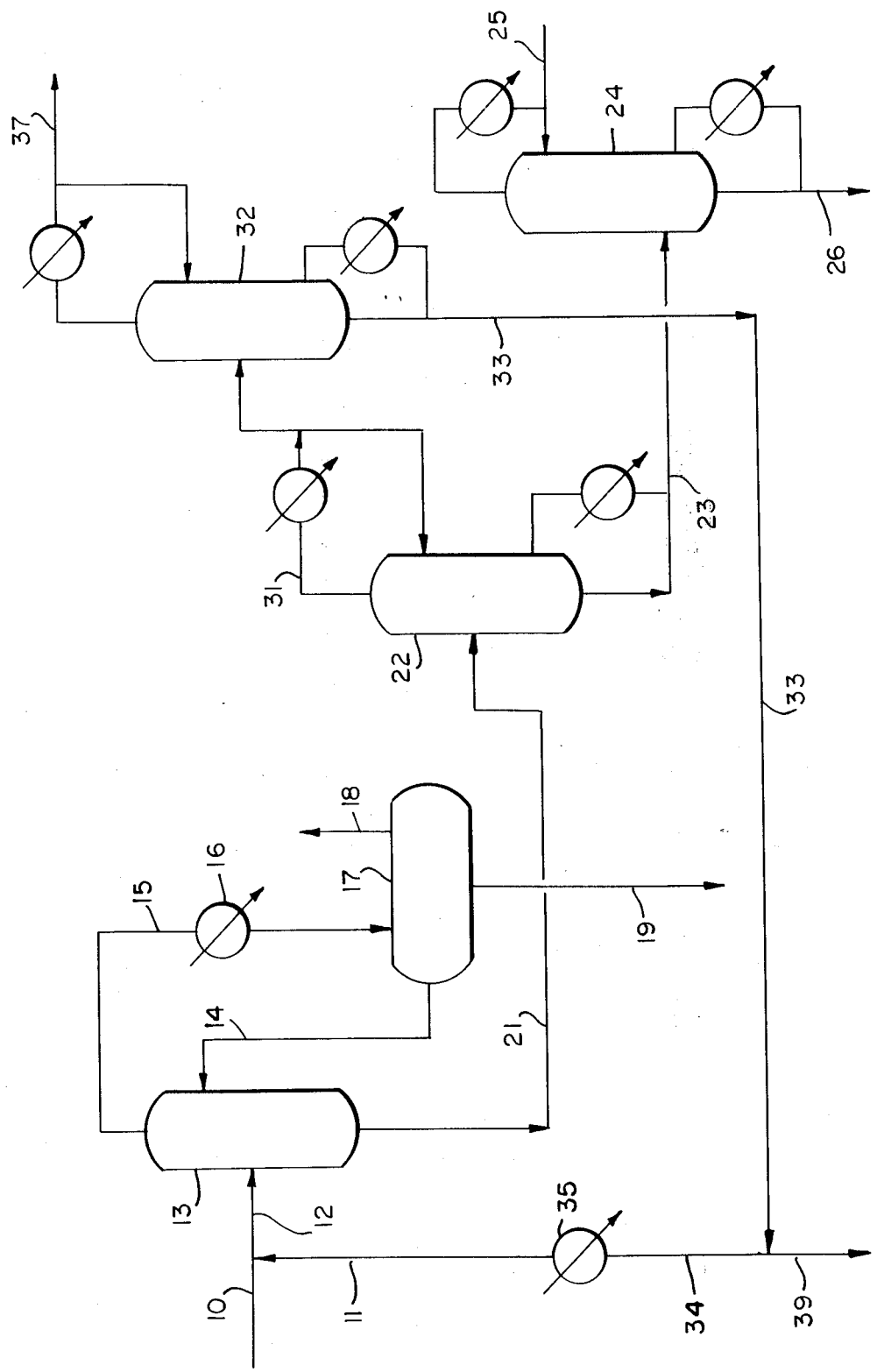

RECOVERY OF TEREPHTHALONITRILE

This invention relates to the recovery of terephthalonitrile (TPN), and more particularly, to a process for separating TPN from a solution which includes p-xylene.

In the production of TPN from p-xylene, the gaseous reaction effluent includes TPN and unreacted p-xylene, as well as reaction intermediate p-tolunitrile and byproduct benzonitrile. In general, TPN is recovered from the effluent by direct quenching to produce a slurry of TPN in the quench liquid. The crude TPN is then recovered by centrifugation or filtration, followed by further purification of the TPN.

The techniques generally employed in the art require solid handling, which is expensive and cumbersome and, accordingly, there is a need for an improvement in the procedures for recovering TPN.

An object of the present invention is to provide for improved recovery of TPN.

Another object of the present invention is to provide for improved recovery of TPN from a TPN production reaction effluent. Another object of the present invention is to provide for effective separation of TPN from p-xylene.

These and other objects of the present invention should be more readily apparent from reading the following detailed description thereof.

In accordance with one aspect of the present invention, TPN is separated from a solution containing TPN and p-xylene by fractional distillation in a fractionating column with p-tolunitrile being present in the fractionating column in amounts sufficient to solubilize TPN in all portions of the column at which the temperature in the column is below the melting point of TPN, whereby TPN can be separated and recovered in liquid form. The p-tolunitrile and p-xylene are recovered as an overhead product from the column.

In accordance with another aspect of the invention, TPN is recovered from a gaseous TPN production reaction effluent, including p-xylene, reaction intermediate p-tolunitrile, and byproduct benzonitrile, by quenching the effluent with a quench liquid containing p-tolunitrile to separate from the gaseous effluent a solution of the TPN in a mixture of p-tolunitrile, benzonitrile and p-xylene. The solution is then introduced into a fractional distillation column, with the p-tolunitrile being present in the column in an amount sufficient to solubilize the TPN in all portions of the column at which the temperature in the column is below the melting point of the TPN, to thereby separate the TPN, in liquid form, from the p-xylene, benzonitrile and p-tolunitrile.

In effecting the separation of the TPN from a solution containing TPN and p-xylene by fractional distillation, the p-tolunitrile is introduced into the column to provide a weight ratio of p-tolunitrile to TPN introduced into the column of at least 3:1 and preferably at least 5:1. As should be apparent, it is possible to employ large excess of p-tolunitrile with respect to TPN; however, such large excesses are not required and increase overall costs. As a result, in general, the weight ratio of p-tolunitrile to TPN introduced into the column generally does not exceed 15:1, and most generally does not exceed 10:1. The fractional distillation is effected at temperature and pressure conditions such that p-tolunitrile and xylene as well as other light components present in the feed; e.g., benzonitrile, can be recovered as overhead, with the TPN being sufficiently soluble in the p-tolunitrile containing liquid at the top of the column, whereby the TPN does not separate as a solid in the top of the column. In general, the fractional distillation is effected at an overhead temperature from about 300° F. to about 450° F., a bottoms temperature from about 450° F. to about 600° F., and a total pressure from 300 mm Hg absolute to 10 psig. The above conditions are illustrative and the selection of optimum conditions is deemed to be within the scope of those skilled in the art from the teachings herein.

A solution which includes TPN and p-xylene which is fractionated in accordance with the present invention to recover liquid TPN, as hereinabove described, is generally recovered from a TPN production gaseous reaction effluent, which includes TPN and unreacted p-xylene as well as reaction intermediate p-tolunitrile and byproduct benzonitrile. In accordance with this aspect of the invention, the gaseous reaction effluent is directly contacted with a quench liquid containing p-tolunitrile, which may or may not include p-xylene, to condense TPN from the effluent as a solution in p-xylene and p-tolunitrile, which also includes benzonitrile present in the effluent. The quench liquid employed for condesing the TPN includes sufficient p-tolunitrile for providing the p-tolunitrile requirements for the subsequent recovery of TPN, as a liquid, by fractional distillation, as hereinabove described. It is to be understood, however, that it is not necessary to provide the p-tolunitrile requirements for the fractional distillation during the quench in that additional p-tolunitrile can be added prior to the fractionation.

In general, the TPN is condensed from the effluent at a quench temperature from about 200° F. to about 300° F., and at a pressure of from 0 to about 15psig. It is to be understood, however, that the above conditions are illustrative, and the selection of optimum conditions is deemed to be within the scope of those skilled in the art from the teachings herein.

The TPN production reaction effluent is produced by any one of a wide variety of procedures which involve reaction between p-xylene and ammonia, in the presence or absence of free oxygen, and in the presence of a suitable catalyst. Thus, for example, such a procedure is described in U.S. Pat. No. 3,925,447.

The present invention will be further described with respect to an embodiment thereof, illustrated in the accompanying drawing, wherein:

The drawing is a simplified schematic flow diagram of an embodiment of the present invention.

Referring now to the drawing, a TPN production reaction effluent, including TPN, unconverted p-xylene, ammonia, p-tolunitrile, benzonitrile, carbon monoxide, carbon dioxide, nitrogen, hydrogen cyanide and water vapor, in line 10 is directly contacted with a p-tolunitrile rich recycle stream, in line 11, to effect quench cooling of the reaction effluent in line 12 to thereby condense terephthalonitrile therefrom. The combined stream in line 12 is introduced into a quench tower 13 to effect separation of a solution of TPN in a mixture of p-xylene, benzonitrile and p-tolunitrile. The remaining vapor is contacted in the top of the quench tower 13 with a scrub liquid introduced through line 14 to scrub any remaining TPN from the gas.

A gaseous stream is withdrawn from quench tower 13 through line 15, cooled in cooler 16 to effect condensation of water vapor, p-xylene, p-tolunitrile and benzonitrile, and the mixed stream introduced into a separator 17. A gaseous stream is withdrawn from separator 17 through line 18, and is recycled to the TPN production reactor. An aqueous stream is withdrawn from separator 17 through line 16. An organic stream, containing p-xylene, p-tolunitrile and benzonitrile is recycled as a scrub liquid to the quench tower 13 through line 14.

A solution of TPN in p-xylene and p-tolunitrile, and further including benzonitrile is withdrawn from tower 13 through line 21 and introduced into a fractional distillation column, schematically indicated as 22. As hereinabove described, the feedstream in line 21 contains an amount of p-tolunitrile which is sufficient to maintain the TPN in solution at all points in the fractionator tower 22 at which the TPN is not in molten form.

The fractionating column 22 is operated at a temperature and pressure, as hereinabove described, to separate TPN, as a liquid bottoms, from an overhead of p-xylene, p-tolunitrile and benzonitrile.

A molten TPN bottoms is withdrawn from column 22 through line 23 and may be used directly or further purified by distillation in a column 24 to recover and separate TPN from any heavier components present in stream 23. The further purified TPN product is recovered through line 25 and a heavier component containing stream, containing minor amounts of TPN is recovered through line 26.

An overhead containing p-tolunitrile, p-xylene and minor amounts of benzonitrile is withdrawn from fractional distillation column 22 through line 31 and introduced into a further fractional distillation column 32 to effect fractionation thereof into a p-tolunitrile rich stream and a p-xylene rich stream. A p-tolunitrile rich stream is withdrawn as bottoms from column 32 through line 33 and a first portion thereof passed through line 34 including a cooler 35 for use as quench liquid in line 11. The remaining portion thereof is passed through line 35 for introduction into the TPN production reactor.

A p-xylene rich stream is withdrawn as overhead from column 32 through line 37 for recycle to the TPN production reactor.

Alternatively, the overhead withdrawn from fractionating column 22 can be partially condensed, with the vapor stream being recycled to the TPN production reactor and the condensed liquid stream being employed to provide quench liquid requirements, with the remaining portion thereof being recycled to the TPN production reactor.

As a further alternative, the overhead from fractionator 22 can be totally condensed, with a portion thereof providing the quench requirements in line 11 and the remaining portion being recycled to the TPN production reactor. In such an embodiment, there is selective stripping of p-xylene by the non-condensible gases in the quench operation.

The hereinabove described embodiment may be further modified within the spirit and scope of the present invention and, accordingly, the scope of the present invention is not limited to such an embodiment.

The present invention is particularly advantageous in that it is possible to separate TPN from a solution containing p-xylene without the necessity of solid handling. In accordance with the teachings of the present invention, TPN can be recovered in molten form in that at the conditions prevailing in the top portion of the fractionating column the TPN is sufficiently soluble in the p-tolunitrile containing liquid that solid TPN is not separated from solution, thereby avoiding column plugging. Moreover, at a few trays below the top of the column, the temperature conditions are such that the TPN is in molten form.

In recovering TPN from a TPN production reaction effluent, p-tolunitrile is effectively built up in the feed to the fractionator by recycling p-tolunitrile as a quench liquid to provide the amount of p-tolunitrile required for effecting the separation of TPN without solid separation.

Numerous modifications and variations of the present invention are possible in light of the above teachings and, therefore, within the scope of the appended claims, the invention may be practiced otherwise than as particularly described.

What is claimed is:

1. A process for separating terephthalonitrile from a solution containing terephthalonitrile and p-xylene, comprising:

introducing a solution containing terephthalonitrile and p-xylene and p-tolunitrile into a fractional distillation column, said p-tolunitrile being present in an amount sufficient to solubilize the terephthalonitrile in all portions of the fractional distillation column at which the temperature in the fractional distillation column is below the melting point of terephthalonitrile; and recovering terephthalonitrile in liquid from the fractional distillation column.

2. The process of claim 1 wherein the weight ratio of p-tolunitrile to terephthalonitrile introduced into the column is at least 3:1.

3. The process of claim 2 wherein the solution further includes benzonitrile.

4. The process of claim 3 wherein the column is operated at an overhead temperature of from 300° to 450° F. and a bottoms temperature of from 450° to 600° F.

5. A process for recovering terephthalonitrile from a gaseous terephthalonitrile production effluent, comprising:

directly contacting a terephthalonitrile production gaseous effluent containing terephthalonitrile and p-xylene with a quench liquid containing p-tolunitrile to separate from the gaseous effluent a solution containing terephthalonitrile, p-tolunitrile and p-xylene;

introducing said solution into a fractional distillation column, said solution containing an amount of p-tolunitrile which is sufficient to solubilize the terephthalonitrile in all portions of the fractional distillation column at which the temperature in the column is below the melting point of terephthalonitrile; and recovering from said fractional distillation column terephthalonitrile in liquid form.

6. The process of claim 5 wherein the effluent further contains p-tolunitrile and benzonitrile, and said solution introduced into the fractional distillation column further contains benzonitrile.

7. The process of claim 6 wherein an overhead containing p-tolunitrile, benzonitrile and p-xylene is recovered from the fractional distillation column and a portion of said overhead is employed as the quench liquid.

8. The precess of claim 7 wherein p-tolunitrile is introduced into the column in an amount to provide a p-tolunitrile to terephthalonitrile weight ratio of at least 3:1.

9. The process of claim 8 wherein the fractional distillation column is operated at an overhead temperature of from 300° to 450° F. and a bottoms temperature of from 450° to 600° F.

* * * * *